(12) United States Patent
Parihar et al.

(10) Patent No.: US 7,497,823 B2
(45) Date of Patent: Mar. 3, 2009

(54) FLEXIBLE SHAFT STABILIZING DEVICES WITH IMPROVED ACTUATION

(75) Inventors: Shailendra Parihar, Coopersburg, PA (US); Steven Nguyen, North Brunswick, NJ (US); Anthony Miksza, Bethlehem, PA (US); James C. Hart, Basking Ridge, NJ (US); Dan Gordon, Newtown, PA (US)

(73) Assignee: Ethicon, Inc., Somerville, NJ (US)

( * ) Notice: Subject to any disclaimer, the term of this patent is extended or adjusted under 35 U.S.C. 154(b) by 607 days.

(21) Appl. No.: 10/881,982

(22) Filed: Jun. 30, 2004

(65) Prior Publication Data

US 2006/0004250 A1 Jan. 5, 2006

(51) Int. Cl.
*A61F 2/00* (2006.01)

(52) U.S. Cl. ........................................ 600/37
(58) Field of Classification Search .............. 600/37, 600/132, 104, 201, 16, 213, 215, 228–230, 600/210; 606/206, 235, 198; 70/283, 224, 70/275; 403/322.1; 128/897
See application file for complete search history.

(56) References Cited

U.S. PATENT DOCUMENTS

| | | | |
|---|---|---|---|
| 5,976,080 A | 11/1999 | Farascioni et al. | |
| 6,406,424 B1 | 6/2002 | Williamson, IV et al. | |
| 6,464,629 B1 * | 10/2002 | Boone et al. | 600/37 |
| 6,676,597 B2 | 1/2004 | Guenst et al. | |
| 6,730,020 B2 * | 5/2004 | Peng et al. | 600/201 |
| 6,935,805 B2 * | 8/2005 | O'Brien et al. | 403/322.1 |
| 7,018,328 B2 * | 3/2006 | Mager et al. | 600/37 |
| 2002/0077532 A1 | 6/2002 | Gannoe et al. | |
| 2003/0088150 A1 | 5/2003 | Green, II et al. | |
| 2003/0158463 A1 * | 8/2003 | Julian et al. | 600/104 |
| 2003/0229271 A1 * | 12/2003 | Briscoe et al. | 600/229 |
| 2004/0015047 A1 | 1/2004 | Mager et al. | |

FOREIGN PATENT DOCUMENTS

| | | |
|---|---|---|
| WO | WO 02/054937 A2 | 7/2002 |
| WO | WO 03/061484 A1 | 7/2003 |

* cited by examiner

*Primary Examiner*—Charles A Marmor, II
*Assistant Examiner*—Christine D Hopkins

(57) ABSTRACT

A stabilizing device having a flexible shaft with a terminal connector and surgical tools used therewith. The flexible shaft is responsive to a tension element connected to a distal end of the shaft and in communication with a proximal end of the shaft. An elastic means interfacing between the proximal end of the tension element and an actuating cam cause the shaft to adapt for differences in activating tension between straight and curved positions. Accordingly, stretching and deformation of the tensioning element is reduced and shaft stiffness upon activation of the tensioning element is repeatable. The terminal connector includes a ball-and-socket arrangement adapted to resiliently absorb movement of an organ during surgery. A bendable suction stabilizer foot adaptable to contours of an organ is also provided as an attachment to the stabilizer device.

29 Claims, 8 Drawing Sheets

FLEXIBLE SHAFT STABILIZING DEVICES WITH IMPROVED ACTUATION

BACKGROUND OF THE INVENTION

1. Field of Invention

The invention relates to the field of surgical instruments, and more specifically to improvements in flexible shaft stabilizer devices and surgical tools usable in conjunction therewith.

2. Description of Related Art

In the field of medical instrumentation, flexible shaft stabilization devices are known in the art. Such devices are sold under the name OCTOPUS by the MEDTRONIC company and AXIUS by the GUIDANT company. Particularly in Coronary Artery Bypass Graft (CABG) procedures, such devices are used to stabilize the surface of the beating heart muscle at the site where an anastomosis will be formed. The devices commonly have a malleable shaft of a certain length, with a stabilizer foot or other apparatus at a distal end of the shaft. The apparatus is positioned as required, then a lead screw at a proximal end of the shaft is turned by some manner of handle to secure the shaft rigidly in place. The turning of the lead screw commonly applies tension to a fiber, such as a metal wire or braided cable. Tensioning of the cable compresses the flexible shaft, and secures it rigidly into an intended straight or curved position. These devices are considered an improvement over other stabilizers, because the length of the shaft can be positioned away from the surgical field, as compared to fixed-arm stabilizers that may impede access and vision to the surgical site.

These devices are not without drawbacks, however. Among the drawbacks are difficulties with tensioning the fiber or cable that compresses the flexible shaft. It has also been observed that after the first actuation of the shaft in such devices, subsequent actuations with equal turning of the actuator as the first actuation did not achieve the desired or necessary stiffness to hold the intended straight or curved position of the shaft. Further, currently available shafts are often not conducive to convenient positioning of the distal end of the flexible shaft at the surgical site by the surgeon, even when the shaft is in the relaxed state. Further, still detrimental wearing and gall can occur at the cam of the tensioning mechanism, including the generation of metal particulate that may compromise an otherwise sterile surgical field. Turning of the handle to tension the fiber and position the shaft appropriately is also a time consuming and cumbersome task often requiring assistance from a second medical professional. A great deal of force is typically required to actuate the handles of known flexible shaft devices having high shaft stiffness.

In addition to the drawbacks of known flexible shaft devices, a surgical apparatus secured to a distal end of a flexible shaft, or even a rigid retractor, may have its own drawbacks. A suction device for grasping and manipulating tissue such as those sold by the MEDTRONIC company under the brands STARFISH or URCHIN, or those sold by the GUIDANT company under the brand XPOSE may be used with a flexible shaft. The former lack the ability to dynamically adapt to moving tissue, such as the beating heart, however, and rely instead on the resiliency of the material comprising the suction device to better conform to the targeted tissue. The latter, on the other hand, are awkward, difficult to manipulate, and prone to user error.

Another apparatus that may be used in conjunction with a flexible shaft, though also with other devices, is a bendable suction bridge. Suction bridge stabilizers are used to immobilize tissue at a surgical site, for example the surface of the beating heart. These bridge devices typically place a stabilizing arm on either side of the target vessel, and use downward pressure to immobilize the tissue. Suction may be provided to secure the tissue to the stabilizer. However, it is desirable to position the suction devices perpendicularly to the heart surface, which itself is curved, the particular curvature individual to each patient. Rigid devices cannot accommodate this curvature in the heart. Moreover, is cumbersome to provide a suction line individually to each arm, however, as is commonly done in such devices. Likewise, it is desirable to avoid obstructing the vessel between the arms of the bridge, as a flat transverse bridge of known bridge devices might do.

Some devices in the prior art, including those sold under the OCTOPUS and ACROBAT brands, do not present a bendable bridge, and are therefore less able to adapt to the variety of tissue configurations a surgeon finds in practice. Others, such as those sold under the FLEXITE brand, are bendable at the bridge but not at the pods surrounding the arms, and require multiple vacuum inlets to each arm. Accordingly, an improved suction foot device that better conforms to the targeted tissue is desirable in the art.

BRIEF SUMMARY OF THE INVENTION

The present invention provides an improved design in the flexible shaft of a stabilizing device and surgical tools used therewith. Particularly, the current invention addresses the problem of the marginally longer tensioning element that often occurs when the shaft is in a straight position.

According to the present invention, a stabilizing device having a flexible shaft is provided. The flexible shaft has a tension element secured to a distal end of and in communication with a proximal end of the flexible shaft. A cam positioned at the proximal end of the flexible shaft is operative to displace a proximal end of the tension element. A lever is operative to displace the cam, and elastic means interface between the proximal end of the tension element and the cam to displace the shaft as desired. Ideally, the stabilizing device is operative by a single medical professional.

An elastic means, or spring mechanism, is provided at a proximal end of the shaft to absorb the tension force applied to the tensioning element when the handle is actuated to lock the shaft in a rigid position. In this manner the tensioning element, or cable, does not get stretched as much and permanent deformation of the tensioning element is minimized even when numerous activations of the handle are performed. Higher repeatability of positioning a rigid shaft in a desired position is thus more readily achieved. The spring mechanism also provides improved flexibility in the shaft by permitting a gap to occur at the proximal end of the tensioning element, or cable, between the uncompressed spring and a radial flange when the handle is not actuated and the shaft is in its relaxed state. In this manner, the shaft may accommodate more surgical environments by unlocking the tensioning element, without compromising the rigidity of the shaft by locking the tensioning element when desired.

Additionally, the present invention provides a terminal connector for holding a surgical tool apparatus to a distal end of the flexible shaft. The terminal connector provides rotational movement to the surgical tool according to the beating of the heart, or other movements of an organ the tool is attached to. The terminal connector comprises a socket providing at least a portion of a spherical surface in its interior, a ball sized to fit within the interior of the socket, the ball having an axial hole extending at least partially therethrough, a stem extending outward from the ball and having a flange adjacent one end, the flange being retained in the axial hole, and an elastic means within the axial hole acting on the flange. The surgical tool held at the terminal connection may be a suction cup device or other device for use with the flexible shaft according to the invention.

Additionally, the present invention provides a bendable suction stabilizer foot for use with the flexible shaft. The bendable stabilizer foot comprises at least two bendable arms extending from a bendable bridge, each arm having a fluid passage in fluid communication with a bendable suction pod having at least one outlet thereon, a flexible passage connecting the at least two fluid passages, and an inlet in fluid communication with at least one fluid passage. Alternately, a bendable suction stabilizer foot comprises at least two bendable arms, each arm having a fluid passage within itself and at least one outlet thereon, a bendable bridge passage connecting the at least two fluid passages, and an inlet in fluid communication with at least one fluid passage. The bendable stabilizer foot is attached to the flexible shaft by the terminal connection.

BRIEF DESCRIPTION OF THE DRAWINGS

These and other features, aspects and advantages of the present invention will be made apparent with reference to the following description and accompanying figures, wherein like reference numerals refer to like structures across the several views, and wherein.

DETAILED DESCRIPTION OF THE INVENTION

Experimentation has shown that for the certain shaft size and cam mechanism under test, using a wire-braided cable as a tension element, pre-loaded with 150 lbs of tension in a rigid straight configuration required 340 lbs. of tensile load to activate in a curved configuration. This additional loading exceeded the elastic limit of the cable, and stretched the cable by 0.06 in., which stretching degraded the shaft stiffness of subsequent activations. To accommodate for this, this invention provides an elastic means allowing compliance in the flexible shaft device without stretching the tension element.

Figure 1:
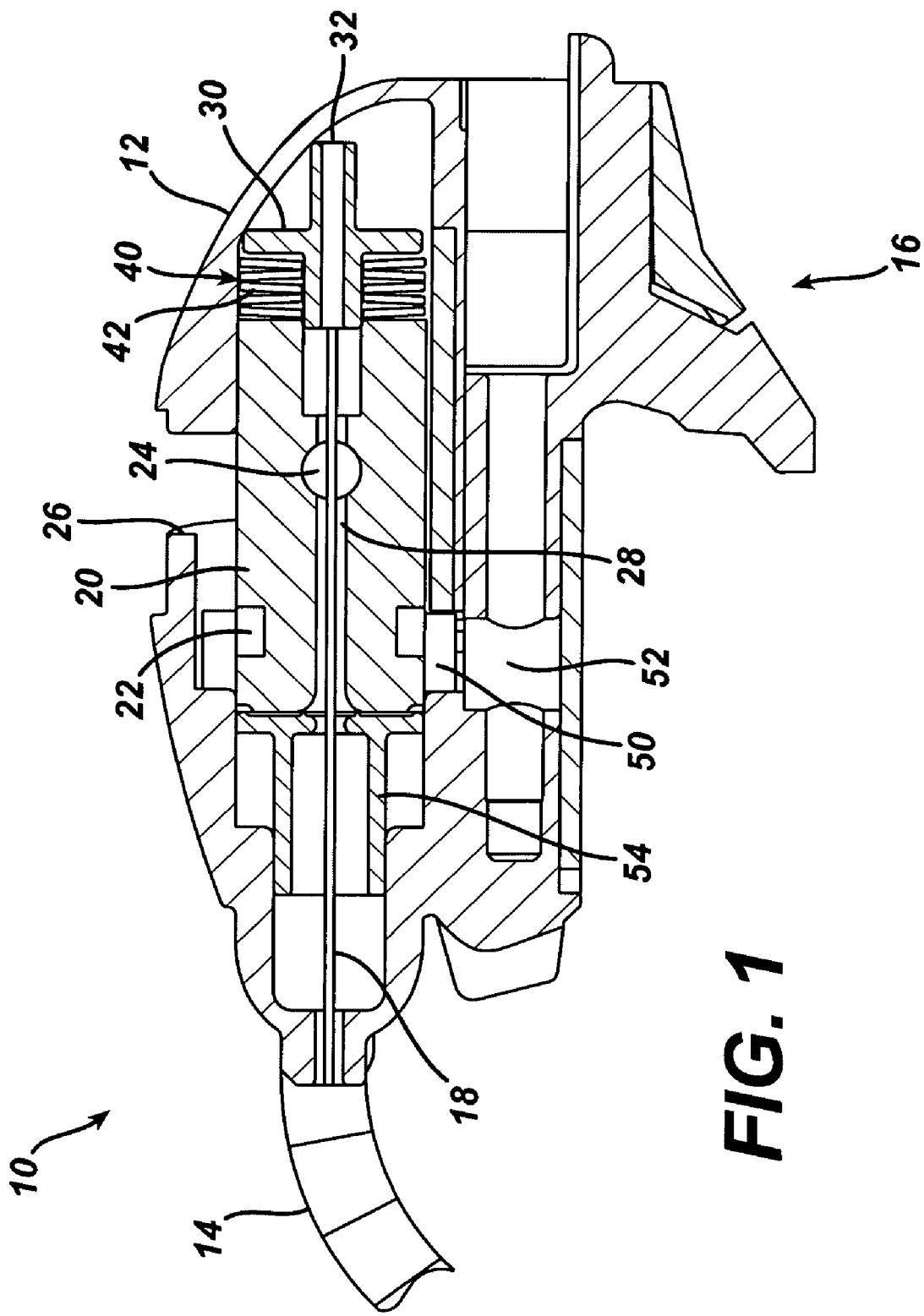
FIG. 1 illustrates a cross-sectional view of the stabilization device according to one embodiment of the invention.

Turning now to FIG. 1, shown is the proximal base 12 of the flexible shaft, generally 10. The shaft portion 14 extends distally from the proximal base 12. The proximal base 12 may include a mounting bracket 16, in this exemplary embodiment along an underside thereof. The mounting bracket 16 facilitates the use of the flexible shaft 10 in conjunction with a retractor, rib-spreader or other thoracic surgical apparatus in a manner generally known in the art.

The flexible shaft 10 includes a tension element 18. The tension element may be a braided cable having strands of metal and/or other material, exclusively or in combination, or a single filament of metal or other material known in the art, which is both flexible and suitable to transmit a tensile load along a length of the flexible shaft 10. The tension element 18 is secured at a distal end of the shaft portion 14 and is in communication with a proximal end of a cam 20, generally, though not exclusively, via a longitudinal passage therethrough. An alternate embodiment of the shaft portion 14 is disclosed in the commonly assigned co-pending patent application Ser. No. 10/736,199, entitled VARIALE STIFFNESS SHAFT, filed 15 Dec. 2003, the complete disclosure of which is hereby incorporated herein by reference for all purposes.

In operation, a proximal end of the tension element 18 is displaced proximally to transition the shaft portion 14 from a relaxed to a rigid state. To achieve this displacement, this exemplary embodiment has a cylindrical cam 20. The cylindrical cam 20 includes a cam groove 22 round its outer surface, which works in cooperation with one or more cam followers (not shown) to displace the cam as it is rotated about its cylindrical axis. A transverse through hole 24 may be present to receive a lever 25 (See FIG. 5) to obtain mechanical advantage and assist in the rotation of the cylindrical cam 20. The lever may extend beyond the body of the proximal base through opening 26 provided for that purpose. Alternate embodiments of the cam mechanism are disclosed in the commonly assigned U.S. Pat. No. 7,241,264, entitled VARIABLE-PITCH CAM MECHANISM FOR TENSION DEVICES, filed 30 Jun. 2003, the complete disclosure of which is hereby incorporated herein by reference for all purposes.

The tension element 18 extends to a proximal terminus 32. The cylindrical cam 20 has an axial passage 28 to facilitate the interface of the tension element 18 with the cylindrical cam 20. A radial flange 30 may be secured to the tension element 18 at its proximal terminus to facilitate the interface with the cylindrical cam 20. For example, the flange 30 may be crimped, soldered, or welded to the tension element, as would be apparent to one of ordinary skill. An elastic means 40 provides an interface between the radial flange 30 and the cylindrical cam 20. As shown in the embodiment of FIG. 1, the elastic means 40 may comprise one or more disk springs 42. In some embodiments, five (5) disk springs 42 are formed of 301 stainless steel each have a OD of 0.472 in., an ID of 0.165 in., a thickness of 0.024 inches, and a free height of 0.039 in., compressing to a solid height equal to their thickness. As an alternate 17-7 steel may be used, notwithstanding potential for corrosion. In other embodiments, disk springs 42 of 17-7 steel may be provided with surface treatment to prevent corrosion. As illustrated, disk springs 42 are preferably arranged in alternating directions, though they need not be. Neither must each disk spring 42 of a plurality comprising an elastic means 40 be identical. This configuration may be varied in accordance with the requirements of stiffness in the flexible shaft 10 and the space available in the proximal base 12. In still other embodiments, the elastic means 40 comprises one or more coil springs, and/or one or more elastomeric elements, as will be described.

The elastic means 40, or spring mechanism, is provided at a proximal end of the cam 20 to absorb this tension force applied to the tensioning element 18, when the tensioning element is actuated to lock the shaft 14 in a rigid position. When actuated, tensile force applied to the tensioning element 18 by the action of the cam 20, is absorbed by deformation in the elastic means 40. In this manner stretching or permanent deformation of the tensioning element 18, or cable, is minimized even when numerous activations are performed. Higher repeatability of positioning a rigid shaft in a desired position is thus more readily achieved. The spring mechanism also provides improved flexibility in the shaft by permitting a gap (g) (see FIGS. 4C, 4D) to occur at the proximal end of the tensioning element, or cable, between the uncompressed spring and a radial flange 32 when the shaft is in its relaxed state. In this manner, the shaft portion 14 may be manipulated about the surgical environment by unlocking the tensioning element 18, without compromising the rigidity of the shaft when locking the tensioning element 18 as desired.

To provide the gap (g), the elastic means 40 is preferably designed to deform less than the total displacement of the cam 20. The difference between the total displacement of the cam 20 and the cumulative deformation of the elastic means 40 provides flexibility in to the shaft portion 14 in its relaxed state. Greater difference provides a larger gap (g), and greater flexibility of the shaft portion 14 in the relaxed state. Increasing numbers of spring elements also decreases the activation force necessary because the spring rate decreases with the increase in spring numbers. However, the size and/or number of spring elements is constrained by the space available within the proximal base 12.

Figure 2:
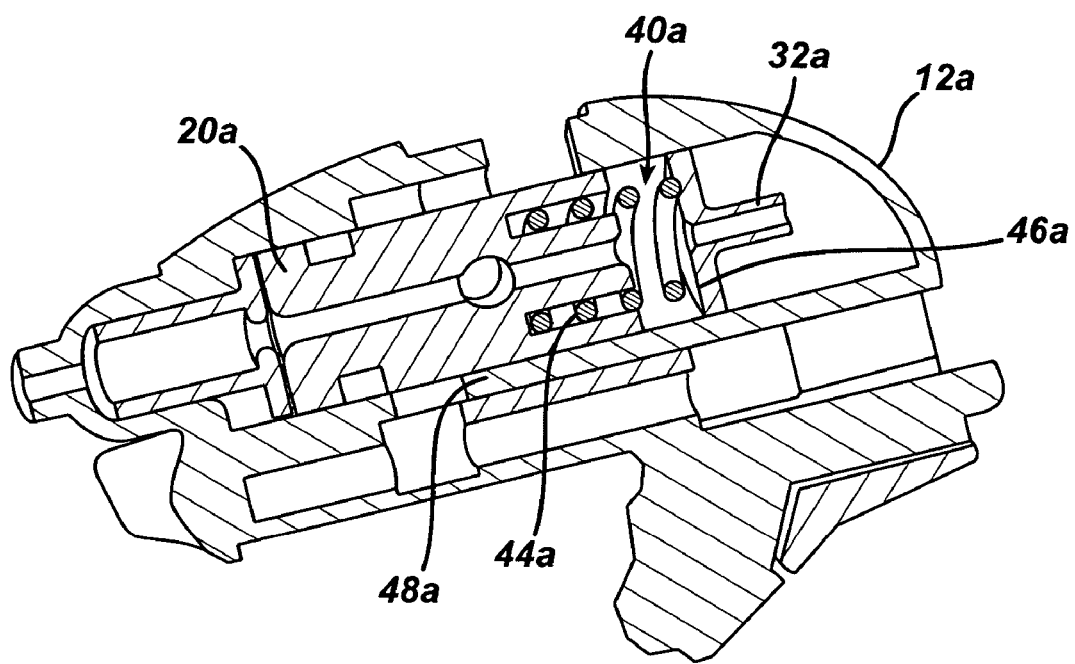
FIG. 2, illustrates another embodiment of the stabilization device in cross-section according to the invention.

Referring now to FIG. 2, an embodiment of the stabilizing device having a coil spring 40a, as elastic means 40 is shown. A relief 44a is provided in the cylindrical cam 20a in order to accommodate the coil spring 40a while reducing the overall axial length of the cam. In addition, a key 46a on the radial flange 32a is shown in FIG. 2. Key 46a engages a keyway 48a provided in proximal base 12a to prevent rotation of the radial flange 32a along the axial travel of the cylindrical cam 20a. This key and keyway may be provided in other embodiments as well. The exemplary coil spring 40a of FIG. 2. is formed of 301 Stainless steel and has an OD of 0.375 in, and ID of 0.2 in., a wire diameter of 0.083 in., a free length of 0.55 in., and a solid length of 0.37 in., which gives a spring rate of 1,100 lbs./in. As an alternate, 17-7 steel may be used for the coilspring 40a, notwithstanding potential for corrosion. The embodiment shown in FIG. 2 is otherwise similar to that shown in FIG. 1.

Figure 3:
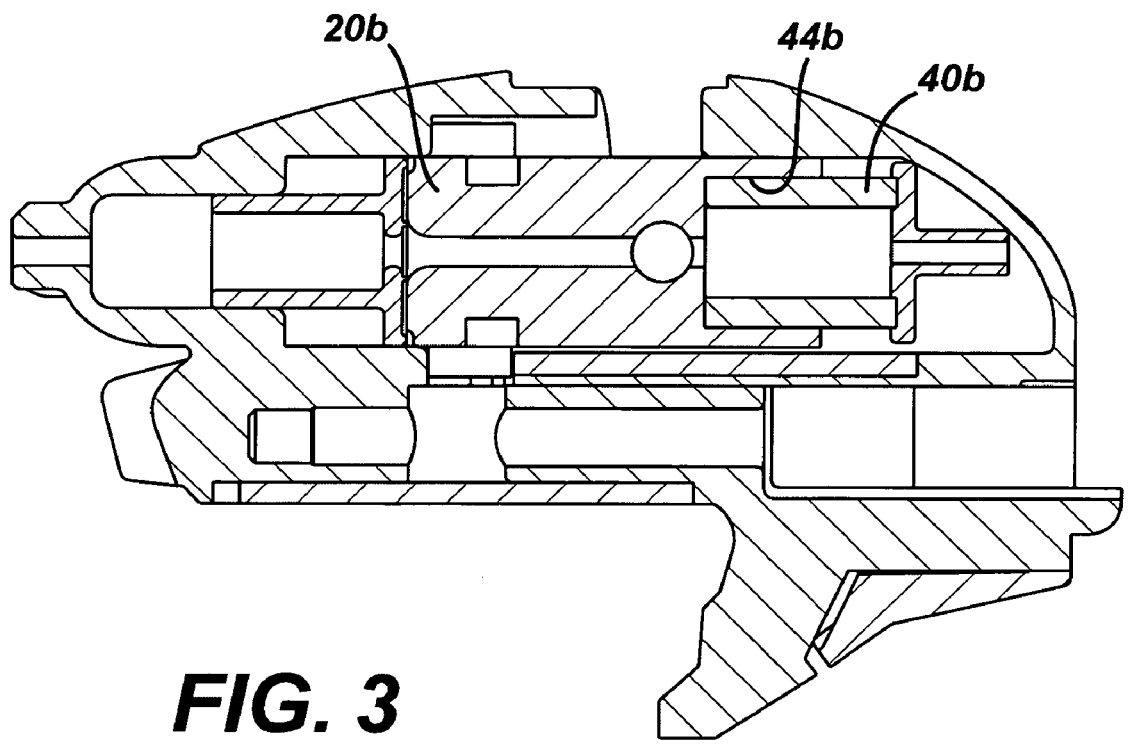
FIG. 3 illustrates another embodiment of the stabilization device in cross-section according to the invention.

Referring to FIG. 3, another embodiment of the stabilizing device is shown. The stabilizing device of FIG. 3 has an elastomer element 40b as elastic means 40. Similar to the embodiment of FIG. 2, a relief 44b is provided in the cylindrical cam 20b in order to accommodate the elastomer element 40b while reducing the overall axial length of the cam of FIG. 3. The elastomer element 40b may comprise urethane, or a material exhibiting similar compressive yield characteristics. The stabilizing device of FIG. 3 is otherwise similar to that shown in FIG. 1.

Figure 4A:
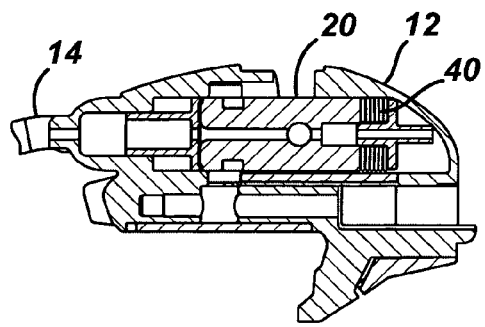
FIGS. 4A-D illustrate the operation of the flexible shaft of the stabilization device of FIG. 1.
Figure 4B:
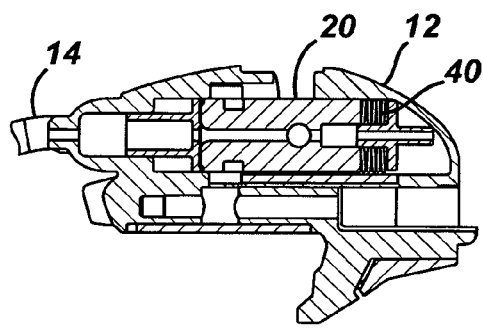
Figure 4C:
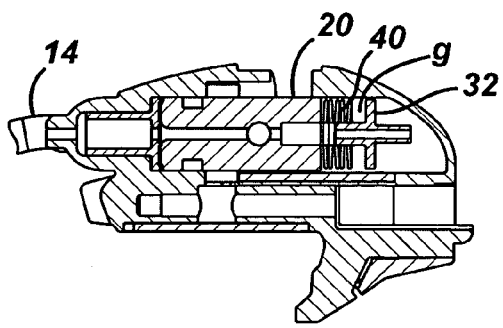
Figure 4D:
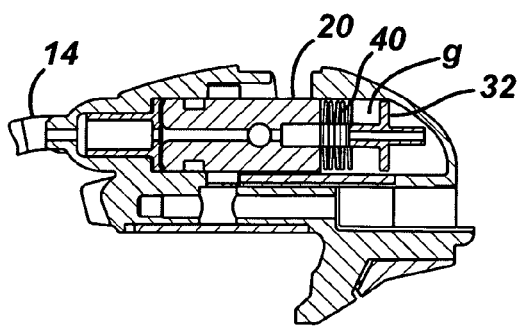

The operation of the flexible shaft 10 will be explained with reference to FIGS. 4A-D and the embodiment of FIG. 1. FIG. 4A illustrates the position of the cylindrical cam 20 with the shaft portion locked in a curved position. Note that the elastic means 40 is nearly fully compressed. Compare this to FIG. 4B, which illustrates the position of the cylindrical cam 20 with the shaft portion locked in a straight position. Note that in FIG. 4B, the elastic means is not as fully compressed as in FIG. 4A, the curved position. Moving on to FIGS. 4C and 4D shown is the position of the cylindrical cam 20 with the shaft portion 14 unlocked in curved and straight positions, respectively. Note that in both cases, the elastic means 40 is uncompressed. The gap (g) induced between the radial flange 32 and the elastic means 40 may vary between the straight and curved positions as seen in the figures. This gap, indicating an unloading of the elastic means 40, gives added flexibility to the shaft portion in the relaxed state. The tensile force in the tensioning element 18 is proportional to the deformation in the elastic means 40. In a curved, locked position, the elastic means 40 prefereable is at its maximum deformation. Accordingly, the tensile force in the tensioning element 18 is also maximized in this state, which provides desirable rigidity to the shaft portion 14 when locked in a curved position.

Referring again to FIG. 1, the cylindrical cam is guided by a friction plate 54 to smooth the cam actuation. Friction plate 54 is preferably formed of a Nylon Resin, such as ZYTEL 101 L, however the friction plate may also be formed of a 300 series Stainless steel. A cam ring 50 includes one or more cam followers (not shown) that follow the cam groove 22 of cylindrical cam 20. The outer surface 52 of the cam ring 50 may be knurled to assist in maintaining its location in the proximal base 12. The cam followers carry the axial load of the tension element 18, and may be subject to wearing and galling. To minimize this effect, the cam followers can preferably comprise 440C Stainless steel, tempered to a Rockwell C hardness of about 56. Additionally, the cylindrical cam 20 may be formed of 316 steel, exhibiting a Rockwell B harness of 91. Alternately, the materials may be exchanged, the cam followers of 316 steel and the cylindrical cam 20 of 440C Stainless steel. Additionally, the surface finish of either or both of the cam followers and the cam groove 22 may be polished in order to further reduce friction and/or wear. However, beyond a certain surface finish, increased polishing can promote detrimental galling. The balance of reduced friction and galling will be taken into account by those skilled in the art in selecting an parropriate surface finish for a given application.

Moreover, a lubricant may be introduced on the rubbing surfaces, cam followers and cam groove 22. For example, DOW CORNING DC-360, which is a biocompatible medical fluid, having a viscosity of about 1,000 to about 12,000 centistokes may be used as the lubricant. DC-360 is a preferred lubricant over the also-acceptable DOW CORNING DC-111, which is a silicone grease whose very high-viscosity was less effective in reducing friction than the DC-360. In addition to prolonging the life of the mechanism, the reduced friction at the cam followers improved the ease of actuating the mechanism, thereby improving overall performance.

Variable stiffness shafts are typically used in combination with certain surgical tools carried on a distal end thereof. More particularly, the variable stiffness flexible shaft is used to position such surgical tools at the surgical site, and to maintain the position of such surgical tools through the rigidity of the shaft when actuated. Certain among these tools direct a negative suction pressure to hold the heart in a desired position for a better approach to the surgical site.

For example, during a CABG surgery, it is commonly necessary to access the surface beneath the heart. It is also known to use a suction cup device to hold a portion of the heart, typically the apex, to lift the beating heart muscle. The suction cup device must be capable of holding the heart muscle in an elevated position notwithstanding the beating motion of the heart. It is also desired that the surgical tool, such as the suction lifting device, attach to the variable stiffness shaft to facilitate the grasping and positioning of the suction cup or other surgical tool on the heart. The artisan should appreciate that the suction cup device may be used on other organs as well.

Figure 5:
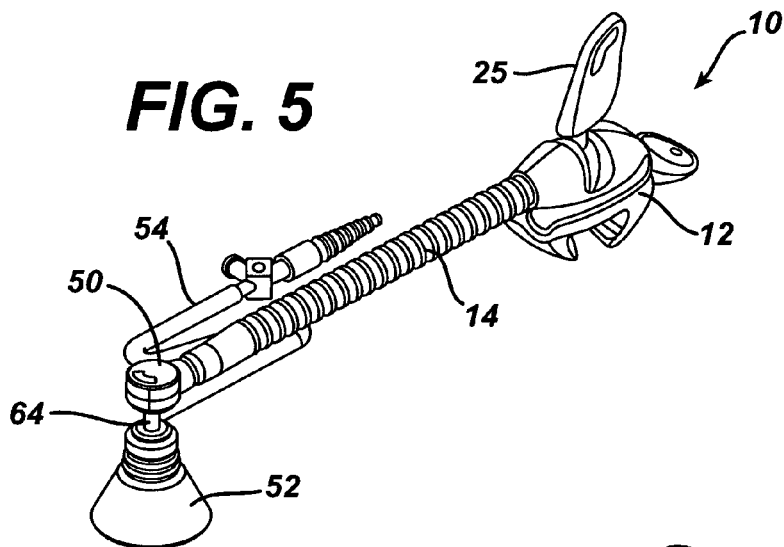
FIG. 5 illustrates a flexible shaft having a terminal connector according to another aspect of the invention.

Referring now to FIG. 5, shown is a flexible shaft 10 as described, for example, with reference to FIG. 1. A terminal connector 50 is positioned at a distal end of shaft portion 14. The terminal connection 50 connects suction cup 52 to the shaft portion 14 via stem 64. A suction conduit 54 extends proximally from an inlet 66 (see FIG. 6) projecting from the stem 64.

Figure 6:
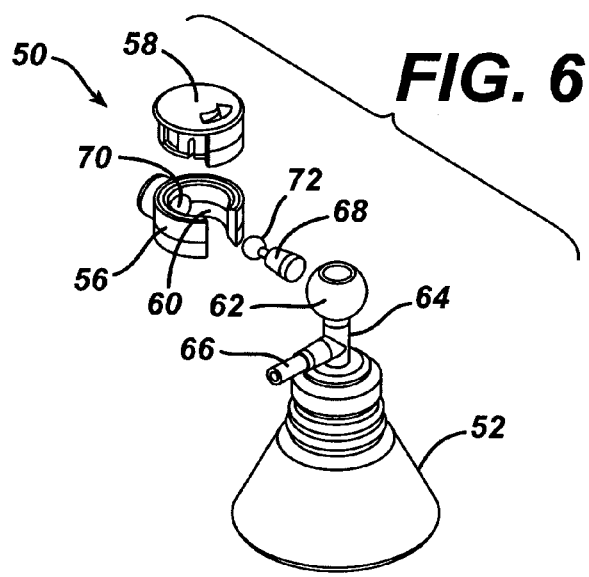
FIG. 6 illustrates the terminal connector of FIG. 5 in partially exploded assembly view.

Referring now to FIG. 6, the terminal connector 50 is illustrated in a partially exploded assembly view. Terminal connector 50 comprises a ring 56 and a cap 58. An interior surface of the ring 56 comprises a portion of a spherical surface 60. The interior of cap 58 (not shown) likewise comprises a portion of a spherical surface. The assembled ring 56 and cap 58 form a socket that accepts ball 62. Extending from the ball 62 is a stem 64, connecting the ball with suction cup 52. Positioned on the stem 64 is an inlet 66 for introducing vacuum pressure, as from suction conduit 54 (see FIG. 5). Conduit 54 need not provide suction, but instead could provide air, oxygen, or any fluid generally, as a routing conduit to the distal end of the flexible shaft, as would be apparent to one of ordinary skill in light of the desired application.

Referring still to FIG. 6, a ball 72 is provided on one end of the mounting rod 68 passes through hole 70 in the ring 56 for connection to the shaft portion 14. As assembled, ring 56 is generally free to rotate around mounting rod 68. Alternately, the mounting rod 68 may be configured to restrict rotation of the ring 56 after the shaft portion 14 is activated to a rigid state. In the latter example, mounting rod 68 and hole 70 would both be at least slightly conically shaped, and/or have surfaces designed to engage to restrict motion, the activation of tension element 18 initiating the restriction.

The ring 56 and cap 58, as assembled, provide a handhold to grasp the assembly forming the ball-and-socket connection, and may be provided with a friction-enhancing surface for that purpose. Furthermore, by positioning the suction inlet 66 below the terminal connector 50, the likelihood of improperly grasping the inlet 66, and potentially releasing the suction conduit 54, is reduced.

Figure 7:
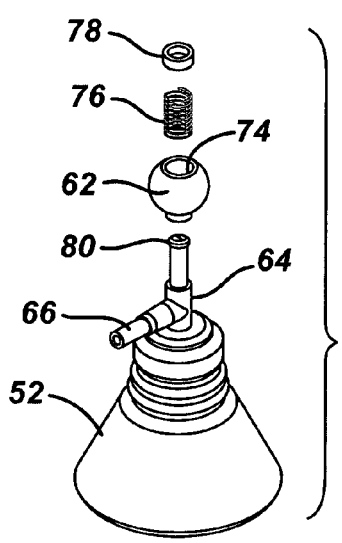
FIG. 7 illustrates the terminal connecter of FIG. 5 in additional detail in a further exploded assembly view.

Referring now to FIG. 7, shown is the suction cup 52, stem 64, and ball 62 in a further exploded assembly view. A flange 80 is positioned adjacent one end of stem 64, and is inserted through hole 74 in ball 62. The fit may be an interference fit, to capture the flange 80 within the ball 62. Alternately a closure may be provided as is known in the art. An elastic member 76, shown as a coil spring, is inserted into the hole 74, and engages the flange 80. In alternate embodiments, elastic member 76 can be an elastomer compression element, a disk spring, a trapped gas spring assembly, or other compliant device. The elastic member 76 may bias the flange upward and/or downward, and may engage the flange 80 from above and/or below. A closure 78, in this case a ring, but alternately a cap, is provided to retain the elastic member 76 within the ball 62.

Referring to FIGS. 5-7 once assembled, the suction cup 52 is positioned on the organ and the suction pressure applied. Most commonly, the cup 52 is placed on the apex of the heart, though other organs and locations may be engaged by the suction cup device. The ball 62 is free to rotate inside the ring 56 and cap 58. Ring 56 is free to rotate about the axis of mounting rod 68. Additionally, the suction cup 52 and stem 64 are free to move axially under the bias of elastic member 76. Each of these allow the device to hold the heart in position while accommodating the beating motion of the heart.

Figure 8:
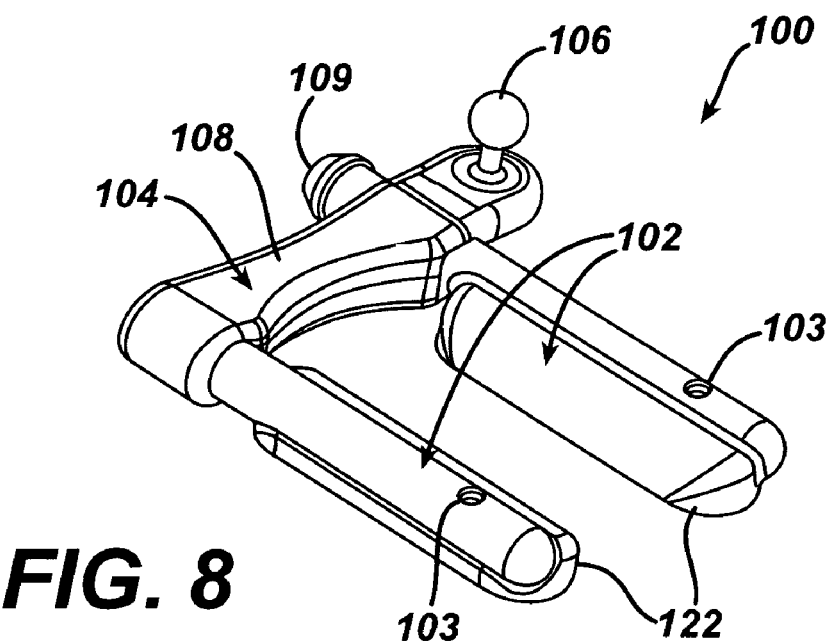
FIG. 8 illustrates a suction foot stabilizer device according to another aspect of the present invention.

Referring now to FIG. 8, shown is a suction foot stabilizer device, generally 100. A stabilizer foot is used, for example, to immobilize a portion of the heart surface for the attachment of a bypass graft to a coronary artery during a beating-heart surgery. Foot 100 comprises two arms 102 connected to a bendable bridge member 104 having opposed ends and an outer covering 108. The arms 102 are generally positioned along either side of the target coronary artery. The arms 102 each comprise internal pod passages 103. A fluid inlet 109 admits suction pressure to the passages 103. Bendable will be taken in its ordinary sense, and malleable will be taken to mean bendable in a fashion that generally holds its bent configuration when a bending force is removed, e.g., as a metal material might. Components described as bendable may also be malleable.

A mounting ball 106 is provided to attach the foot 100 to the terminal connector of a flexible shaft, a retractor, or other surgical positioning or stabilizing device as described with reference to FIGS. 1, and 4-6 for example. Each arm 102 includes a bendable pod 122, that allows the arms to shape and conform to the curvature of the heart surface. Suction provided to arms 102 through the inlet 109 is directed through passages 103 to malleable suction pods 122. The malleable suction pods 122 additionally have outlets on an underside thereof to engage the heat tissue surface to further immobilize the surgical site.

Figure 9:
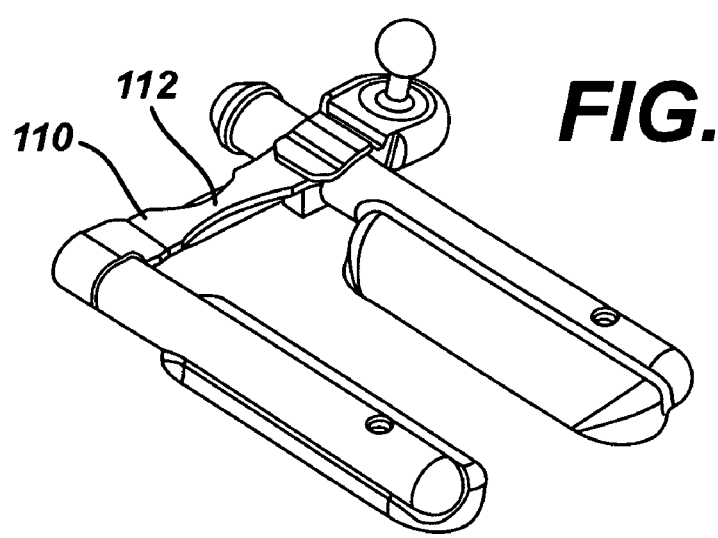
FIG. 9 illustrates the suction foot stabilizer device of FIG. 8 in partial cutaway view.

Referring now to FIG. 9, the outer covering 108 (FIG. 8) having been removed, a bridge link member 110 is shown. The bridge link member 110 is generally stamped from an annealed metal plate. The reduced dimension neck 112 between the extremities of the bridge link 110 facilitates bending the bendable bridge 104 to form an arch connecting the arms 102 according to the contours of the heart, or other organ, the stabilizing foot is engaged with. Additionally, each arm may be made to perpendicularly engage to the surface of the patient's heart, notwithstanding the curvature of the heart surface.

Figure 10:
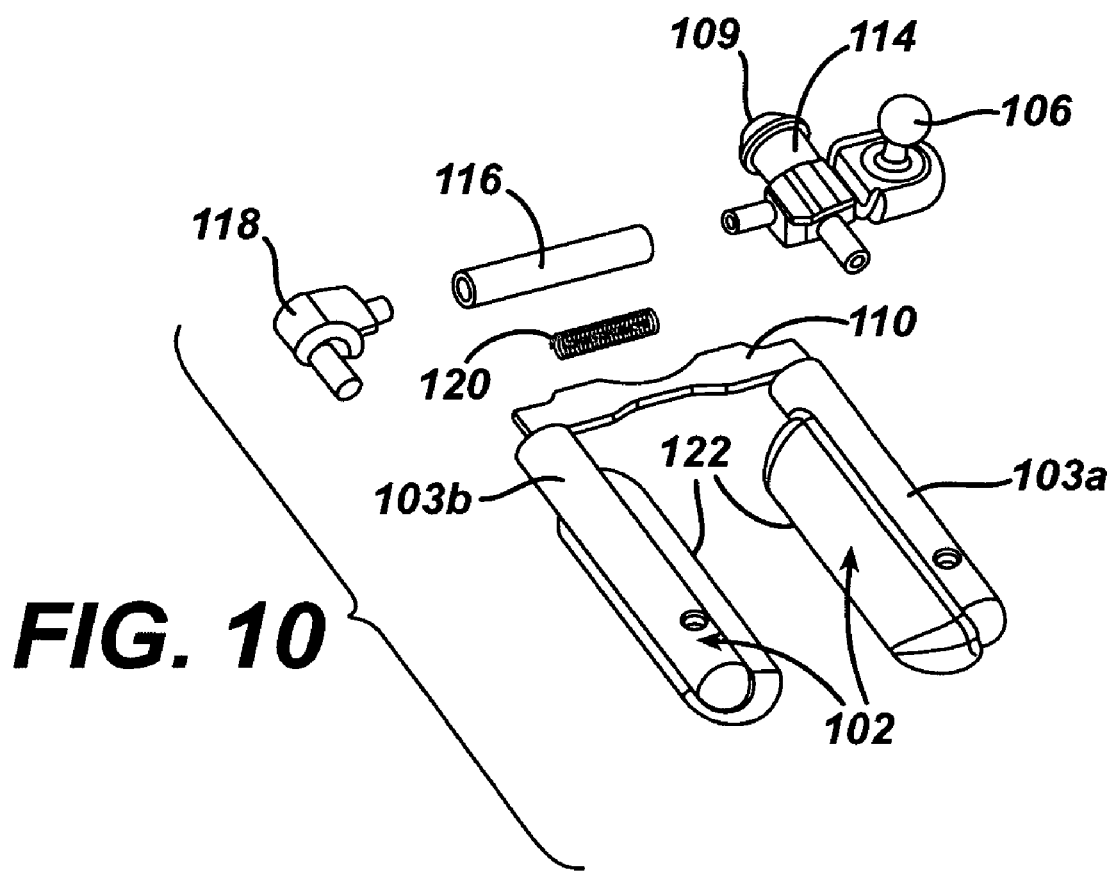
FIG. 10 illustrates the suction foot stabilizer device of FIG. 8 in exploded assembly view.

Referring now to FIG. 10, foot 100 is shown in exploded assembly view. Inlet 109 leads to a T-shaped connector 114, connecting a first pod passage 103a with a bridge passage 116. An L-shaped connector 118 connects bridge passage 116 with a second pod passage 103b. Bridge passage 116 may be a flexible or soft plastic tube, or alternately a braided metal tube. A stent 120 that is flexible or bendable, but more rigid than bridge passage 116, may be inserted into the bridge passage 116 to prevent collapse or kinks during the bending process.

Figure 11:
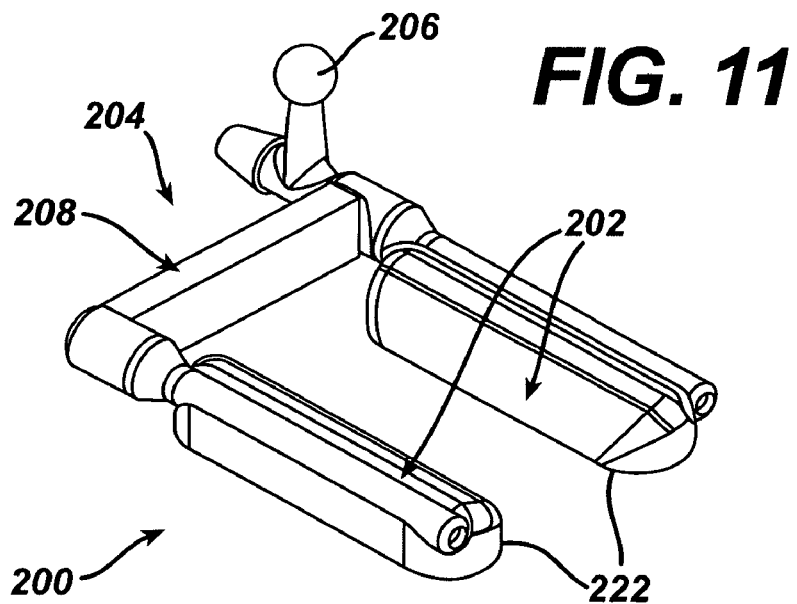
FIG. 11 illustrates an alternate embodiment of a suction foot stabilizer device.
Figure 12:
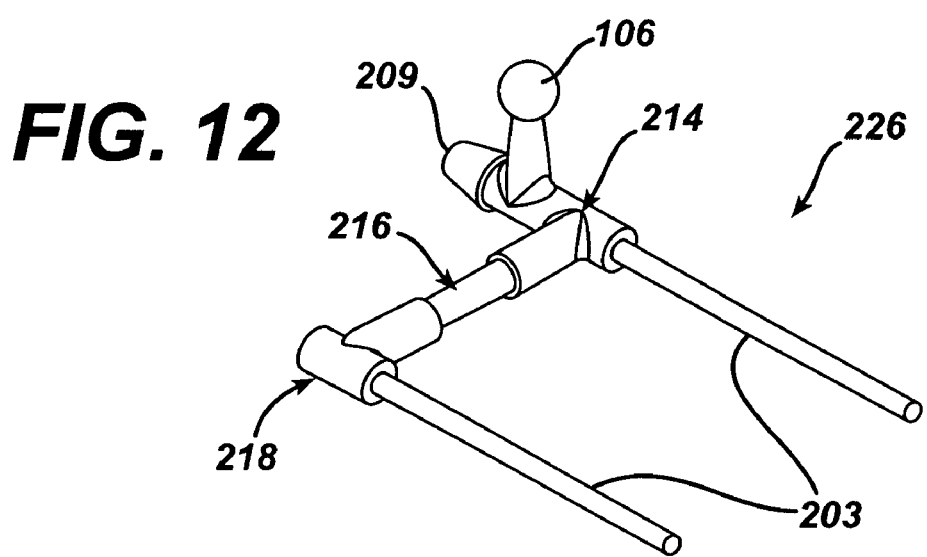
FIG. 12 illustrates the suction foot stabilizer device of FIG. 11 in partial cutaway view.

Referring now to FIG. 11, shown is an alternate embodiment of a suction foot stabilizer device, generally 200. FIG. 12 illustrates in partial cutaway, the suction foot stabilization device of FIG. 11 with a soft bendable covering 208 and bendable suction pods 222 removed. In FIG. 12, shown is a manifold, generally 226, including passages 216, 203, formed of a bendable material. Therefore, arms 202 (FIG. 11) and bridge 204 (FIG. 11) may be bent to conform to the working surface at the surgical site.

In embodiments of the suction foot stabilizer device, some aspect of the arms and bridge are bendable to conform to the surface of the heart muscle. The malleable bridge member thus helps to alleviate obstruction across the target artery or other vessel.

The present invention has been described herein with respect to certain exemplary and/or preferred embodiments. Certain alterations or modifications will be apparent to those of ordinary skill in the art in light of the disclosed invention. The embodiments described are offered as illustrative, and not limiting, on the scope of the present invention, which is defined with reference to the appended claims.

The invention claimed is:

1. A surgical stabilizing device comprising:
  a flexible shaft having a distal end and a proximal end;

a tension element having a first operative length for inducing a rigid position of the flexible shaft and a second operative length for inducing a non-rigid position of the flexible shaft;

a cam positioned at the proximal end of the flexible shaft operative to transition the tension element between the first operative length thereof and the second operative length thereof, wherein the tension element is secured to the distal end of the flexible shaft and in communication with the proximal end of the cam; and elastic means interfacing between the proximal end of the tension element and the cam, the elastic means contacting a proximal end of the cam and compressing by actuation of the cam and tensioning element to position the flexible shaft in the rigid position, and de-compressing by release of the cam and tensioning element to position the flexible shaft in the non-rigid position.

2. The stabilizing device according to claim 1, wherein the elastic means comprises one or more of a disk spring, a coil spring, and an elastomer spring.

3. The stabilizing device of claim 1, wherein a gap provided at the proximal end of the tension element between the elastic means and a radial flange connected to the tension element, increases flexibility of the flexible shaft when in a flexible state.

4. The stabilizing device according to claim 1, wherein the cam is a cylindrical cam having a cam groove on its outer surface which engages at least one cam follower provided in a base of the stabilizing device.

5. The stabilizing device according to claim 4, further comprising a lever extending radially from the cam and operative to axially rotate the cylindrical cam and displace the tension element.

6. The stabilizing device according to claim 4, wherein at least one of the cylindrical cam and the cam followers comprises one or more of a 316 steel and a 440C stainless steel.

7. The stabilizing device according to claim 1, further comprising a flange connecting a proximal end of the tension element with the elastic means.

8. The stabilizing device according to claim 7, wherein said flange comprises a key which translates in a keyway provided in a proximal base of the flexible shaft to prevent rotation of the flange in an axial direction of travel of the cam.

9. The stabilizing device according to claim 1, wherein the cam comprises one or more of a 316 steel and a 440C stainless steel.

10. The stabilizing device according to claim 1, further comprising a biocompatible lubricant provided on the cam surface.

11. The stabilizing device according to claim 10, wherein the biocompatible lubricant has a viscosity of between about 1000 and about 12,000 centistokes.

12. The stabilizer device of claim 1, further comprising a terminal connector for holding a surgical apparatus to a distal end of the flexible shaft, the terminal, connector providing rotational movement to the surgical apparatus for accommodating movements of an organ the surgical apparatus is engaged with.

13. The stabilizing device of claim 12, wherein the terminal connector further comprises:

a socket having at least a portion of a spherical surface in its interior;

a mounting rod rotatably connecting the socket to the distal end of the flexible shaft;

a ball sized to fit within the interior of the socket and having an axial hole extending at least partially therethrough, the ball rotatably connecting to the socket when received therein;

a stem extending outward from within the ball and having a flange adjacent one end of the stem, the adjacent flange being retained in the axial hole of the ball; and an elastic means within the axial hole acting on the flange.

14. The stabilizing device according to claim 13, wherein the socket of the terminal connector further comprises a ring and a cap, each having at least a portion of a spherical surface in its interior for receiving the ball.

15. The stabilizing device according to claim 14, wherein the portion of the ring has an opening sized to admit the ball into the socket.

16. The stabilizing device according to claim 15, wherein the cap completes the opening in the ring.

17. The stabilizing device according to claim 13, wherein the stem further comprises a passage extending from the stem as an inlet in fluid communication with a vacuum for providing suction to the surgical apparatus.

18. The stabilizing device according to claim 13, wherein the elastic means of the terminal connector comprises one or more of a disk spring, a coil spring, and an elastomer spring.

19. The stabilizing device according to claim 18, further comprising means to restrict the rotation of the socket about the mounting rod.

20. The stabilizing device according to claim 18, wherein the mounting rod passes through a hole in the socket.

21. The stabilizing device according to claim 19, wherein the mounting rod further comprises a ball for attachment to the distal end of a variable stiffness flexible shaft.

22. The stabilizing device of claim 12, further comprising a bendable suction stabilizer foot, the stabilizer foot comprising:

a bendable bridge having opposed ends;

an arm extending from each end of the bendable bridge, each arm surrounded by a bendable pod and having a fluid passage therein and at least one outlet therefrom;

a flexible passage extending though the bridge and connecting the fluid passages of each arm;

an inlet in fluid communication with a vacuum source and at least one fluid passage; and a ball for attaching the stabilizing foot to the terminal connector.

23. The bendable suction stabilizer foot according to claim 22, further comprising a stent located coaxially with the flexible passage.

24. The bendable suction stabilizer foot according to claim 22, wherein the bendable bridge comprises a stamped metal bridge link.

25. The bendable suction stabilizer foot according to claim 24, wherein the stamped metal bridge link has a reduced dimension neck between its extremities.

26. The bendable suction stabilizer foot according to claim 22, wherein the at least one outlet of each fluid passage is adjacent a lower side of each arm.

27. The bendable suction stabilizer foot according to claim 22, wherein the flexible passage further comprises one of a flexible plastic tube and a braided metal tube.

28. The stabilizing device according to claim 23, wherein the stent is more rigid than the flexible passage.

29. The stabilizing device according to claim 28, wherein the arms and the flexible passage are malleable.

* * * * *